United States Patent
Reid et al.

(10) Patent No.: US 7,608,841 B2
(45) Date of Patent: Oct. 27, 2009

(54) SYSTEM AND METHOD FOR A FLUORESCENCE EXCITATION AND DETECTION HAVING DISTINCT OPTICAL PATHS

(75) Inventors: Taylor A. Reid, Carlsbad, CA (US);
Roger H. Taylor, San Diego, CA (US);
Kenneth J. Zajac, San Diego, CA (US)

(73) Assignee: Stratagene California, La Jolla, CA (US)

( * ) Notice: Subject to any disclaimer, the term of this patent is extended or adjusted under 35 U.S.C. 154(b) by 0 days.

(21) Appl. No.: 11/451,903

(22) Filed: Jun. 12, 2006

(65) Prior Publication Data
US 2007/0114444 A1 May 24, 2007

Related U.S. Application Data

(60) Provisional application No. 60/689,903, filed on Jun. 13, 2005.

(51) Int. Cl.
*G01N 21/64* (2006.01)
(52) U.S. Cl. .................................. 250/461.1
(58) Field of Classification Search ............. 250/459.1, 250/358.1, 361 R, 362, 363.01, 364, 365, 250/367, 368, 458.1, 461.1, 461.2; 359/368, 359/385, 389, 390
See application file for complete search history.

(56) References Cited

U.S. PATENT DOCUMENTS

| | | | |
|---|---|---|---|
| 5,440,414 A * | 8/1995 | Kersey et al. ............... 398/152 |
| 6,580,081 B1 | 6/2003 | Thorwirth | |
| 6,597,450 B1 * | 7/2003 | Andrews et al. ............ 356/317 |
| 6,866,824 B2 | 3/2005 | Lafferty et al. | |
| 2002/0043626 A1 * | 4/2002 | Booker et al. ............ 250/459.1 |
| 2003/0044855 A1 | 3/2003 | Anderson et al. | |
| 2003/0127609 A1 * | 7/2003 | El-Hage et al. ............. 250/574 |
| 2004/0044271 A1 * | 3/2004 | Stone et al. .................. 600/182 |
| 2004/0239922 A1 | 12/2004 | Modlin et al. | |
| 2004/0239923 A1 | 12/2004 | Adams et al. | |
| 2005/0079603 A1 | 4/2005 | Sandstrom | |
| 2005/0218338 A1 * | 10/2005 | Wulf et al. ................ 250/458.1 |
| 2006/0132878 A1 * | 6/2006 | Curry et al. ................. 359/196 |

OTHER PUBLICATIONS

International Search Report from WO 2006/138261.

* cited by examiner

*Primary Examiner*—David P Porta
*Assistant Examiner*—David S Baker

(57) ABSTRACT

A system and method for fluorescence excitation and detection having distinct optical paths is disclosed. A system for detecting fluorescence comprises a light source that emits an excitation light into an illumination tube; a plurality of collection optics located around an aperture in the illumination tube for collecting fluorescence; and a detector for determining the amount of fluorescence. A method for detecting fluorescence comprises emitting an excitation light from a light source into an illumination tube; directing the excitation light to an excitation filter; illuminating a sample with the excitation light to generate an emission light; and detecting the optical characteristics of the emission light using a plurality of collection optics located around the illumination tube.

17 Claims, 5 Drawing Sheets

SYSTEM AND METHOD FOR A FLUORESCENCE EXCITATION AND DETECTION HAVING DISTINCT OPTICAL PATHS

RELATED APPLICATIONS

This application claims the benefit of U.S. Provisional Application Ser. No. 60/689,903, filed Jun. 13, 2005, the entirety of which is hereby incorporated herein by reference for the teachings therein.

FIELD

The embodiments disclosed herein relate to fluorescence excitation and detection, and more particularly to a system and method for fluorescence excitation and detection having distinct optical paths.

BACKGROUND

Techniques for thermal cycling of DNA samples are known in the art. By performing a polymerase chain reaction (PCR), DNA can be amplified. It is desirable to cycle a specially constituted liquid biological reaction mixture through a specific duration and range of temperatures in order to successfully amplify the DNA in the liquid reaction mixture. Thermocycling is the process of melting DNA, annealing short primers to the resulting single strands, and extending those primers to make new copies of double stranded DNA. The liquid reaction mixture is repeatedly put through this process of melting at high temperatures and annealing and extending at lower temperatures.

In a typical thermocycling apparatus, a biological reaction mixture including DNA will be provided in a large number of sample wells on a thermal block assembly. Quantitative PCR (qPCR) uses fluorogenic probes to sense DNA. Instrumentation designed for qPCR must be able to detect approximately 1 nM of these probes in small volume samples (e.g., approximately 25 μl). The detection method must be compatible with the thermal cycling required for qPCR. The detection method must also be capable of distinguishing multiple fluorogenic probes in the same sample.

Enhancing the sensitivity of fluorescence detection of a qPCR instrument or method improves the usefulness of that instrument or method by enabling detection of DNA sooner, that is, after fewer thermal cycles.

Prior art systems use the same light path for excitation and detection. In those systems excitation light is directed to a beam splitter, which transmits typically about one-half of the excitation light to the sample. Some of the emitted light from the sample comes back to the beam splitter and a portion of that light, typically about one-half, is directed to a detector. By using beam splitters, only about one-half of the light is reflected and transmitted; therefore, only about one-quarter of the signal is measured.

U.S. Pat. No. 5,757,014 to Bruno et al. discloses an optical detection device for analytical measurements of chemical substances. The Bruno et al. device includes an excitation light guide and an emission light guide that share the same optical light path. U.S. Pat. No. 6,563,581 to Oldham et al. discloses a system for detecting fluorescence emitted from a plurality of samples in a sample tray. The Oldham et al. device includes a plurality of lenses, an actuator, a light source, a light direction mechanism and an optical detection system. U.S. Pat. No. 6,015,674 to Woudenberg et al. discloses a system for measuring in real time polynucleotide products from nucleic acid amplification processes, such as polymerase chain reaction (PCR). The Woudenberg et al. device includes a sample holder, an optical interface, a lens, and a fiber optic cable for delivering an excitation beam to a sample and for receiving light emitted by the sample.

Other prior art methods use fiber optics to deliver the excitation light to and collect the fluorescence from the sample. These methods may either use independent fiber optics for each sample or scan the same fiber optics over all the samples. Some methods illuminate the entire collection of samples simultaneously and detect the fluorescence with large area detectors.

SUMMARY

A system and method for fluorescence excitation and detection having distinct optical paths is disclosed. According to aspects illustrated herein, there is provided a system for detecting fluorescence comprising a light source that emits an excitation light into an illumination tube; a plurality of collection optics located around an aperture in the illumination tube for collecting fluorescence; and a detector for determining the amount of fluorescence.

According to aspects illustrated herein, there is provided a detection system for detecting fluorescence from a plurality of samples comprising an illumination tube for receiving an excitation light from a light emitting diode; a plurality of collection optics located around an aperture in the illumination tube for collecting fluorescence; and a photodiode for detecting the amount of fluorescence.

According to aspects illustrated herein, there is provided a system for detecting fluorescence comprising a tube for collecting fluorescence; a light source that emits an excitation light into a plurality of optics located around an aperture in the tube; and a photodiode for detecting the amount of fluorescence.

According to aspects illustrated herein, there is provided a method for detecting fluorescence comprising emitting an excitation light from a light source into an illumination tube; directing the excitation light to an excitation filter; illuminating a sample with the excitation light to generate an emission light; and detecting the optical characteristics of the emission light using a plurality of collection optics located around the illumination tube.

BRIEF DESCRIPTION OF THE DRAWINGS

The presently disclosed embodiments will be further explained with reference to the attached drawings, wherein like structures are referred to by like numerals throughout the several views. The drawings are not necessarily to scale, the emphasis having instead been generally placed upon illustrating the principles of the presently disclosed embodiments.

Figure 1:
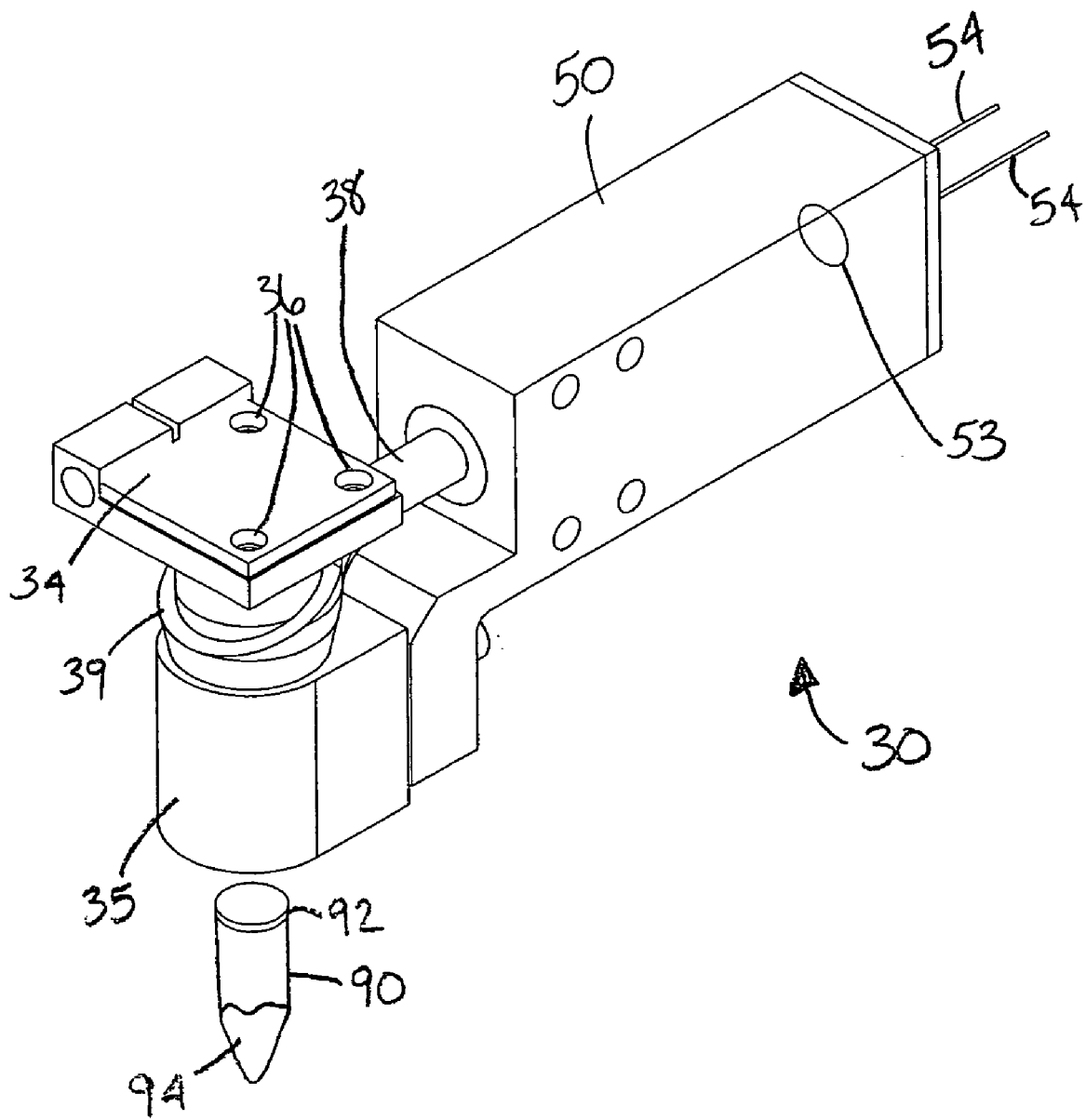
FIG. 1 is a perspective view of an optical module having collection optics located around an illumination tube.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

A system and method for fluorescence excitation and detection having distinct optical paths is disclosed. A system for fluorescence excitation and detection having separate and distinct optical paths is shown generally at 30 in FIG. 1. The system has one optical light path for the illumination (excitation), and a different optical light path for the detection of fluorescence. The optical path for excitation light is free space optics without any collection optics. The optical path for the detection of emitted fluorescence involves collection optics guiding light to a detector. The optical path for detection is outside and around the optical path for excitation.

A light source shines excitation light through a central illumination tube and onto a sample. Illuminating through the central illumination tube allows a compact design and concentrates the light on the sample, minimizing the amount of scattered light. The sample then emits fluorescent light that is detected by a plurality of collection optics located around the illumination tube. Collecting the emitted light at locations around the illumination tube obviates the need for a beam splitter thereby reducing the complexity of the design, eliminating losses from the beam splitter, and reducing the size of the design. The system is compact, and the detected light has both high quality (small amount of scattered light) and quantity (no losses from beam splitters).

When the system is applied to qPCR, the PCR amplification scheme used is not critical, but generally qPCR requires the use of either a nucleic acid polymerase with exonuclease activity or a population of double stranded DNA that increases during the course of the PCR being monitored. Thermal cyclers used in qPCR are typically programmable heating blocks that control and maintain the temperature of the sample through the temperature-dependent stages that constitute the cycles of PCR: template denaturation, primer annealing, and primer extension. These temperatures are cycled up to forty times or more to obtain amplification of the DNA target. Thermal cyclers use different technologies to effect temperature change including, but not limited to, peltier heating and cooling, resistance heating, and passive air or water heating.

As used herein, "optical module" refers to the optics of systems for thermal cycling known in the art including, but not limited to, modular optics, non-modular optics, and any other suitable optics. The optical module can be used for scanning a plurality of samples of biological material after thermal cycling of DNA to accomplish a polymerase chain reaction (PCR), during thermal cycling of DNA to accomplish a quantitative polymerase chain reaction (qPCR), after thermal cycling of DNA after a reverse transcriptase reaction to accomplish a reverse transcription-polymerase chain reaction (RT-PCR), during thermal cycling of DNA after a reverse transcriptase reaction to accomplish a reverse transcription-quantitative polymerase chain reaction (RT-qPCR), or for fluorescence detection during other nucleic acid amplification types of experiments. The optic module controls the illumination light and the detection of fluorescence.

FIG. 1 shows an illustrative optical module 30 having collection optics located around an illumination tube above one of a plurality of sample tubes 90. The optical module 30 is used for detecting fluorescence from a plurality of samples 94 in the plurality of sample tubes 90. The optical module 30 includes at least an optics housing 35, a plurality of collection optics 39, a detector housing 50, and a detector 53. The plurality of collection optics 39 extends down within the optics housing 35 and is located around an illumination tube 44 (shown in FIG. 3). The optical module 30 illuminates from the inside, directing excitation light through the central illumination tube 44, and collects fluorescence from the outside around the illumination tube 44. The plurality of collection optics 39 extends into the detector housing 50. A plurality of leads 54 extend from detector housing 50 connecting the detector 53 to electronics. The electronics both powers a light source and detects the signal from detector 53 in the detector housing 50. The electronics may be remotely attached to the optical module 30. The electronics may be under computer control. The optical module 30 may be a single component or composed of a plurality of assembled parts.

Figure 2:
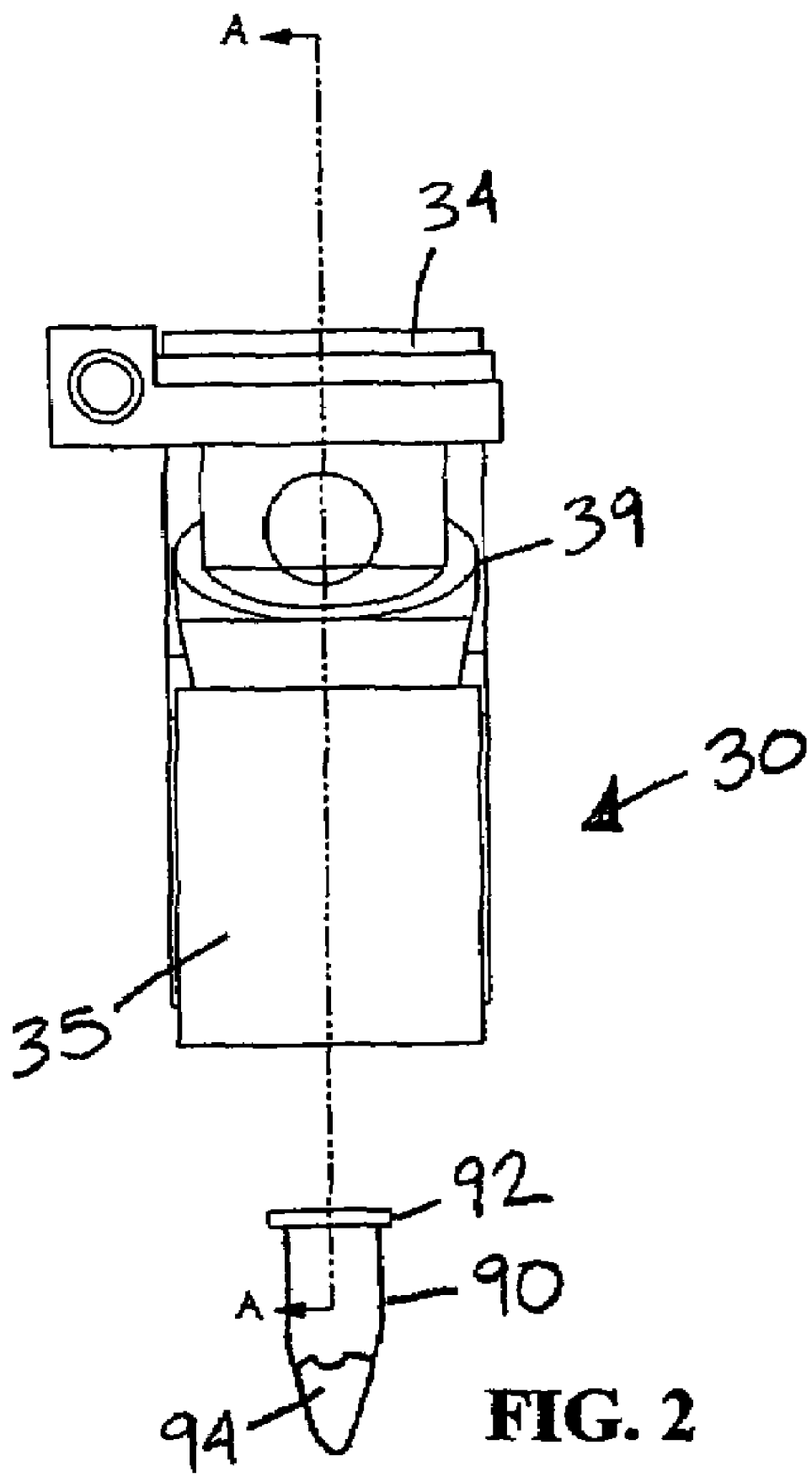
FIG. 2 is a front view of an optical module having collection optics located around an illumination tube.

FIG. 2 is a front view of an optical module 30 having collection optics located around an illumination tube. The optical module 30 is compact, being comparable in size to the sample holders 90 that hold the samples 94 that the optical module 30 measures. The small size of the optical module 30 allows use of a few, small optics, which keeps the overall size and cost of the device low. Use of the same optical module 30 for all samples reduces measurement variability from different samples compared to using different optics for different samples, including optics that illuminate and detect from multiple samples simultaneously.

Figure 3:
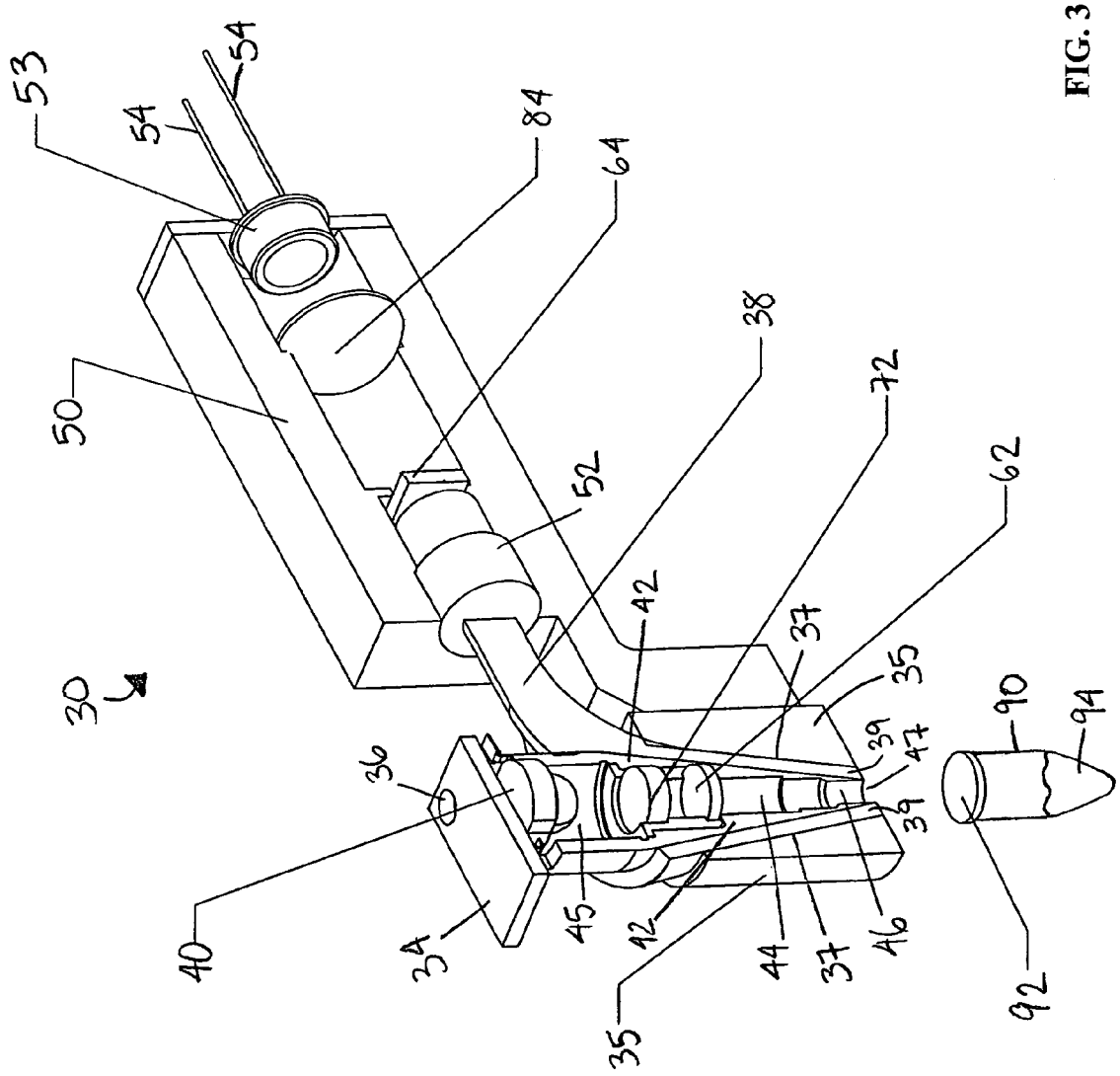
FIG. 3 is a sectional perspective view of an optical module having collection optics located around an illumination tube taken along line A-A in FIG. 2.

FIG. 3 is a sectional perspective view taken along line A-A in FIG. 2 of the optical module 30 having collection optics located around an illumination tube. The optical module 30 collects the fluorescence from the samples through the plurality of collection optics 39 arrayed concentrically around the illumination tube 44. The plurality of collection optics 39 may be either a fiber optic bundle or multiple fiber optic bundles that surround the illumination tube 44. Alternatively, the plurality of collection optics 39 may be fused optical fibers, light pipes, or individual optical fibers that surround the illumination tube 44. Alternatively, the plurality of collection optics 39 may be any type of light guide or guides including, but not limited to, fluid filled fibers or molded plastics. Those skilled in the art will recognize that other types of solid state optics known in the art are within the scope and spirit of the presently disclosed embodiments.

Individual fiber optics can be used to collect light as a concentric ring of collection optics 39 around the illumination tube 44 by packing the individual fiber optics around the illumination tube 44 such that one end of each fiber optic is flush with an aperture 47 of the illumination tube 44. The other ends of the individual fiber optics can be bundled into a ferrule 52 that directs the output of the light collected from the collection ends into a detection module 50. Other methods for collecting light from a concentric ring around an illumination tube may be used, but fabrication of an arrangement of individual fiber optics in a specialized ring may be difficult, expensive, and the fibers may break.

Using fiber optic bundles rather than individual fiber optics could alleviate some of the fabrication and handling concerns. Rather than forming a ring from individual fiber optics, the individual fiber optics could be collected into cylindrical fiber bundles that are arrayed around the aperture 47 of the illumination tube 44. Bundling the fiber optics may provide strength and stability and minimize handling damage.

An assembly of fused fiber optics may also be reliable and easier to handle when manufacturing an instrument that uses collection optics around an illumination tube than an assembly of individual fiber optics. Fused fiber optics consist of individual fiber optics or optical tubes that are bonded together to form a stiff and sturdy monolithic part. Because the fibers or tubes are bonded together over their entire lengths, no stray individual fibers have the possibility to break during handling of the fused fiber optics. In addition, the optical throughput of fused fiber optics is larger than that of individual fiber optics or fiber optic bundles because fused fibers can be packed more tightly than individual fibers, which increases the fraction of the area of the collection optics 39 that actually collects light.

A molded light pipe may also be used for collection of fluorescence. A light pipe is a single, solid piece of optically clear material. The light pipe can be molded from a bulk material, for example, plastic, making fabrication simpler than that of individual fiber optics, fiber optic bundles, or fused fiber optics all of which require assembly from many parts. Because the entire structure of the light pipe transmits light, the fraction of the light pipe collection area that actually collects light is nearly 100%, which is a larger fraction than even fused fiber optics. Because the light pipe consists of essentially only one part, it may be more reliable than individual fiber optics, fiber optic bundles, and fused fiber optics.

An excitation light is produced by a light source 40 mounted to a mounting board 34. A plurality of excitation light rays is emitted from the light source 40 into the illumination tube 44. In FIG. 3, the excitation from the light source 40 is in a downward direction. The light from the light source 40 travels through a lens 72, an excitation filter 62, and then toward the sample tube 90. The light is focused on the inside the sample tube 90, but aiming and focusing the light from the light source 40 onto a cap 92 of the sample tube 90 is effective. Using free space optics for the illumination tube instead of fiber optics enables more compact design because optics for coupling the excitation light into the fiber optics and optics for collimating the excitation light before it reaches the excitation filter are not required. In addition, the excitation light in the free space design can be converging on the sample rather than diverging as it does from fiber optics, which helps reduce scattered light that lowers sensitivity by increasing background.

The lens 72 and/or the illumination tube 44 confines the excitation light into a narrow beam that is coupled preferentially to the sample tube 90. Because the excitation light is focused into the sample tube 90 and the sample 94, there is minimal stray light reflecting throughout the rest of the optical system, which helps keep the background low and the sensitivity high.

The plurality of collection optics 39 surrounds the illumination tube and may cover the remaining area of the opening of the sample tube 90. The plurality of collection optics 39 is designed to maximize collection of light that is emitted from the sample 94. The integration of the plurality of collection optics 39 around the illumination tube 44 provides an efficient two optic system that excites the sample with a small light source, and detects a large area of emitted light. Having the plurality of collection optics 39 located around the illumination tube 44 allows a large detection area for emitted light.

The illumination tube 44 in the center of the plurality of collection optics 39 minimizes the scattering of the excitation light. By ensuring that as much light as possible enters the sample tube 90, less excitation light reflects off the corners and edges of the sample cap 92. Thus, most of the excitation light is coupled into the sample tube 90, wasting only a small amount of the excitation light that does not enter the sample tube 90 and is reflected into the atmosphere. Coupling more light into the sample improves the sensitivity of the module by increasing the signal from the sample. Coupling a higher fraction of the light into the sample improves the sensitivity of the module by increasing the signal while at the same time reducing the background, which limits sensitivity.

The light travels through the cap 92 and into the sample tube 90 where it excites fluorogenic probes typically used in qPCR that are within the sample 94 in the sample tube 90, causing the sample 94 to fluoresce. A biological probe can be placed in each DNA sample so that the amount of fluorescent light emitted as the DNA strands replicate during each thermal cycle is related to the amount of DNA in the sample.

Emitted fluorescent light from the sample 94 passes through the cap 92, and is collected by the plurality of collection optics 39. The fluorescent light travels through the plurality of collection optics 39 around the illumination tube 44. The plurality of collection optics 39 is drawn up and around the illumination tube 44 and grouped in a bundle 38 to converge and enter the detector housing 50. The bundle 38 of collection optics 39 is mounted in the ferrule 52 for attachment to the detector housing 50. The light collected by the collection optics 39 leaves the bundle 38 of collection optics 39 at the ferrule 52 and passes through an emission filter 64, which preferentially transmits signal light and blocks scattered light collected by the collection optics 39. After being transmitted by the emission filter 64, the light collected by the collection optics 39 can be condensed by appropriate optics, in this case a lens 84, onto the detector 53. Reflection optics can also be used to condense the light from the collection optics. The detector 53 converts the intensity of the light into a voltage that is a function of the light intensity. The sense and control electrics for the detector 53 are connected to the detector 53 by the leads 54. By detecting the amount of emitted fluorescent light, the detection system measures the amount of DNA that has been produced. Data can be collected from each sample tube 90 and analyzed by a computer.

In an alternative embodiment, a reflector collects the light exiting the emission filter 64 and reflects the light onto the detector 53. In this embodiment, the reflector is used instead of the lens 84. By replacing the lens 84 with the reflector, the detector 53 could be moved closer to the emission filter 64, resulting in a more compact detector housing 50. The reflector may be conical, toroidal or other geometries known in the art that collect and reflect light.

Figure 4:
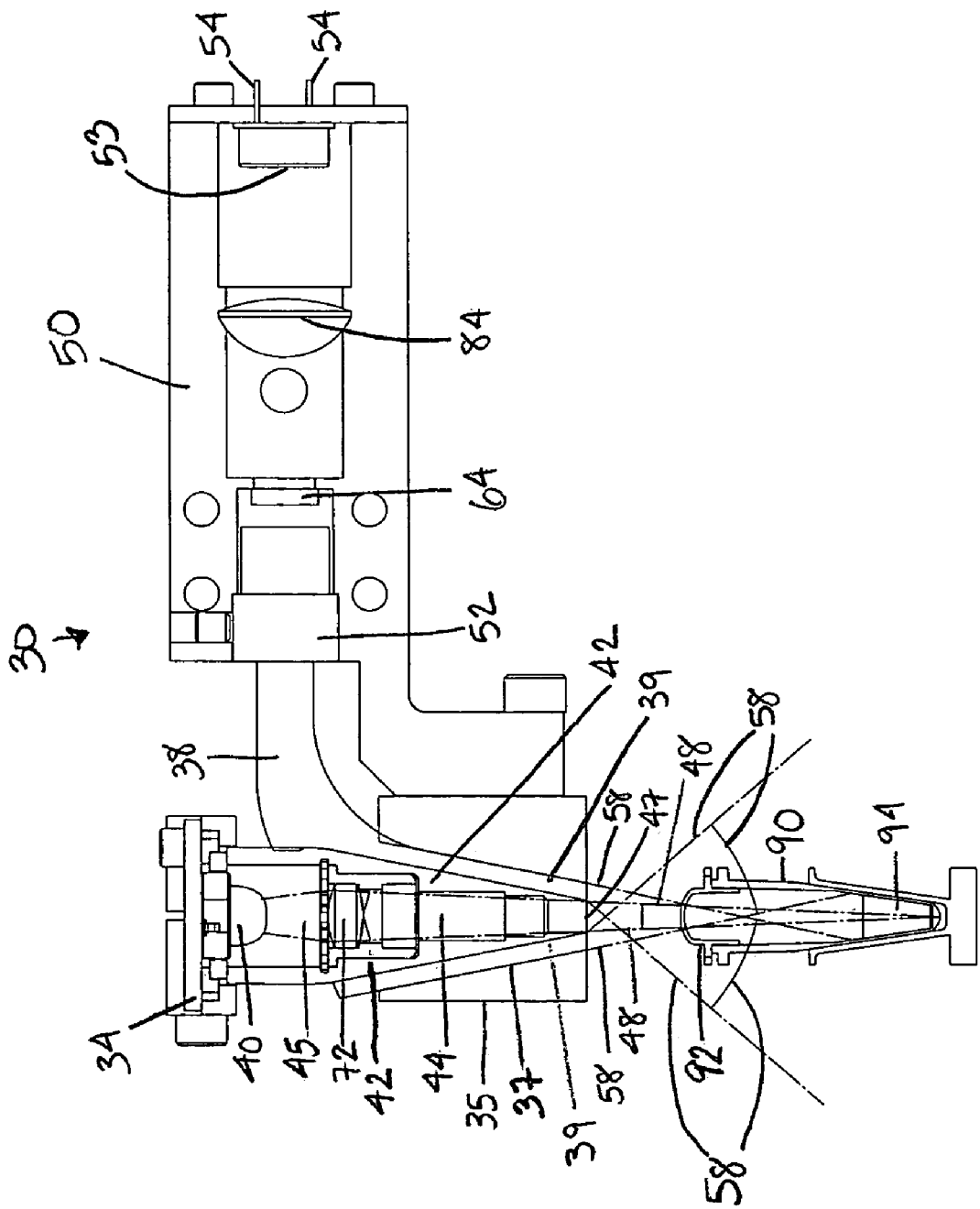
FIG. 4 is a sectional view of an optical module having collection optics located around an illumination tube taken along line A-A in FIG. 2 and showing traces of the light paths.

FIG. 4 is a sectional view of the optical module 30 having the plurality of collection optics 39 located around the illumination tube 44 taken along line A-A in FIG. 2 and showing the area of illumination by an excitation light 48 to the sample 94 and cones of collection 58 of the collection optics 39 for the light emitted from the sample 94. The light source 40 supplies the excitation light 48 for the illumination tube 44. The excitation light 48 travels through the lens 72 that focuses and collimates the excitation light 48. The excitation light 48 then passes through the excitation filter 62, which selects the wavelength of light to excite the sample 94. The excitation light 48 continues through and exits the illumination tube 44 through the aperture 47 and travels toward the plurality of samples 94.

Some of the light transmitted by the cap 92 of the sample tube 90 is absorbed by the sample 94 and excites the fluorogenic probes within the sample, re-emitting light through fluorescence. The re-emitted light (fluorescence) that travels up the sample tube 90, exits through the cap 92, and falls within the cones of collection 58 of the plurality of collection optics 39 concentrically arranged around the illumination tube 44. After the plurality of collection optics 39 collects the fluorescence from the sample 94, the plurality of collection optics 39 transmits the light to the emission filter 64, after which the light is focused by the lens 84 or other suitable optics onto the detector 53.

FIG. 4 illustrates the range of emitted light that is accepted into the plurality of collection optics 39. The plurality of collection optics 39 can accept light incident from a range of angles so long as the light travels in a direction toward the plurality of collection optics 39. Each of the plurality of collection optics 39 can accept light incident from a range of angles defined by the cone of collection 58 in FIG. 4. Because the plurality of collection optics 39 are located around the illumination tube 44, the plurality of collection optics 39 form the cone of collection 58 to collect fluorescence from the sample 94. The plurality of collection optics 39 may be located around 360 degrees around the illumination tube 44.

In an embodiment, the plurality of collection optics 39 partially surrounds the aperture 47 of the illumination tube 44. The plurality of collection optics 39 may be located at distinct positions around the aperture 47 of the illumination tube 44 to maximize the collection of emitted light. In this embodiment, the plurality of collection optics 39 does not completely surround the aperture 47 of the illumination tube 44, and gaps may exist between adjacent collection optics. For example, collection optics may be located every 90 degrees around the excitation light opening, every 45 degrees around the excitation light opening or continuously except for one gap. The spacing between adjacent collection optics may be uniform, varied, or random. Those skilled in the art will recognize that the any number of collection optics and any type of spacing between adjacent collection optics is within the spirit and scope of the disclosed embodiments.

As best shown in FIG. 3 and FIG. 4, the optics housing 35 encloses a portion of the plurality of collection optics 39 and positions the plurality of collection optics 39 around the illumination tube 44. The plurality of collection optics 39 is preferably individual fiber optics arranged in a circular fashion around the illumination tube 44. The plurality of collection optics 39 is placed inside the optics housing 35 in a circular fashion, wrapping around the illumination tube 44. An engagement surface 37 on the interior of the optics housing 35 engages the plurality of collection optics 39. The interior shape of the optics housing 35 positions the plurality of collection optics 39 to arrange and secure the collection optics 39 in a layer on an outside surface 42 of the illumination tube 44. The engagement surface 37 of the optics housing 35 is slanted to create the conical shape of the plurality of collection optics 39 around the illumination tube 44. The optics housing 35 ensures that the plurality of collection optics 39 surround the illumination tube 44 and maintains the conical orientation of the plurality of collection optics 39 around the illumination tube 44.

The illumination tube 44 has a top end 45 that is closed by the light source 40 mounted to the mounting board 34. The illumination tube 44 has a wider diameter at the top end 45 than at a bottom end 46, which allows the illumination optics (the light source 40, the excitation filter 62, and the lens 72) to be contained inside the collection optics 39 and allows the ends of the collection optics to be as close to the center of the illumination tube 44 as possible so as to improve their collection efficiency. The illumination tube 44 acts as a taper so the plurality of collection optics is near to the center of the illumination tube 44. In the conical design, the diameter of the illumination tube 44 decreases from the light source 40 to the aperture 47. The aperture 47 allows the excitation light to exit the illumination tube 44 and flow toward the plurality of sample tubes 90.

As shown in FIG. 3, the plurality of collection optics 39 engage the outer surface 42 of the illumination tube 44 to form an approximately conical shape around the illumination tube 44. A diameter of the plurality of collection optics 39 is greater toward the light source 40 and smaller toward the aperture 47 of the illumination tube 44. The conical design of the plurality of collection optics 39 around the illumination tube 44 allows the plurality of collection optics 39 to be close to the illumination tube 44 at the aperture 47, creating a compact optical module 30. A cylindrical illumination tube is also possible, although it would likely be neither as compact nor as efficient at collecting light from the samples.

The light source 40 is mounted to the underside of the mounting board 34 that contains one or more mounting holes 36. The mounting board 34 may be a circuit board.

The light source 40 may be broad band or narrow band, and it must be bright enough for the optical module 30 to be able to detect the concentration of probes used in the reaction, for example, qPCR.

A light emitting diode (LED) or a plurality of LEDs are particularly suited as the light source 40 because LEDs stabilize quickly, have a compact size, and are available at various wavelengths. An LED is a semiconductor device that emits light through electroluminescence. An LED is a special type of semiconductor diode. Like a normal diode, an LED consists of a chip of semiconducting material impregnated, or doped, with impurities to create a structure called a pn junction. Charge-carriers (electrons and holes) are created by an electric current passing through the junction. When an electron meets a hole, it falls into a lower energy level, and releases energy in the form of light.

LEDs emit incoherent quasi-monochromatic light when electrically biased in the forward direction. The color of light emitted depends on the semiconducting material used and can be near-ultraviolet, visible, or infrared. The wavelength of the light emitted, and therefore its color, depends on the bandgap energy of the materials forming the pn junction. A normal diode, typically made of silicon or germanium, emits invisible far-infrared light, but the materials used for an LED have bandgap energies corresponding to near-infrared, visible, or near-ultraviolet light.

Alternative light sources include, but are not limited to, one or a plurality of laser diodes, lasers, flash lamps, incandescent sources, tungsten halogen lights, or arc sources. Size, heat dissipation, and power limitations, among other factors, should be considered when using alternative light sources.

A laser diode generally refers to the combination of the semiconductor chip that does the actual lasing along with a monitor photodiode chip (used for feedback control of power output) housed in a package. Diode lasers use nearly microscopic chips of Gallium-Arsenide or other exotic semiconductors to generate coherent light in a very small package. The energy level differences between the conduction and valence band electrons in these semiconductors provide the mechanism for laser action. Laser diodes have desirable characteristics such as compactness (the active element is about the size of a grain of sand), low power and voltage requirements, high efficiency (especially compared to gas lasers), high reliability, and long lifetimes with proper treatment.

Unlike LEDs, laser diodes require much greater care in their drive electronics or else they cease operation instantly. There is a maximum current that must not be exceeded for even a microsecond, which depends on the particular device as well as junction temperature.

The light source 40 may be pulsed as disclosed in Assignee's co-pending application Ser. No. 60/677,747, filed May 4, 2005, and application Ser. No. 11/416,886, filed May 2, 2006, the disclosures of which is hereby incorporated herein by reference in its entirety.

The lens 72 focuses the light on the sample tube 90. The optical design should take into account the positions and sizes of the light source 40, the lens 72, the aperture 47, and the sample tube 90. For example, more light can be coupled into the sample tube 90 with a bigger aperture 47, but a bigger aperture means the collection optics 39 are farther from the optical axis of the illumination tube 44, and therefore, collect less emitted light. In addition, the excitation filter 62 performs best when light incident on it is nearly parallel. Thus, the excitation filter 62 should be positioned on the side of the lens having the more nearly parallel light rays.

If used, the filters 62, 64 are preferably narrow band-pass filters that attenuate frequencies above and below a particular band. The filters are preferably a matched pair of filters, consisting of the excitation filter 62 and the emission filter 64. The excitation filter 62 transmits light that excites a particular fluorogenic probe of interest and effectively blocks light that excites other probes or is the same or nearly the same wavelength as the fluorescence emitted by the fluorogenic probes. The emission filter 64 transmits light from the same, excited fluorgenic probe efficiently, but blocks light from other probes and the excitation light effectively. The specifications of the filters depend on the light source. For example, because an incandescent source has a broader spectrum than an LED source, the filters used with an incandescent source need to attenuate a larger range of wavelengths than the filters used with an LED source.

For the emission filter 64 to select the correct wavelength of light for detection, the light should be parallel or at least not diverging by more than about a 20° half-angle upon entering the emission filter 64. The divergence of the light exiting the collection optics 39 is determined by the numerical aperture (NA) of the optics. The lower the NA, the less the light diverges. If the collection optics 39 consists of fiber optics, those fiber optics can be chosen to have a low NA. Alternatively, other optics, for examples lenses, can reduce the divergence of the light from the collection optics 39 before the light reaches the emission filter 64.

After the light passes through the emission filter 64, the lens 84 condenses the light on the detector 53. Because the ratio of signal light to background light is determined primarily by the pair of filters 62 and 64, once the light emitted by the sample is transmitted by the emission filter 64, as much of it as possible should be detected by the detector 53. The lens 84 or other condensing optics should be chosen to maximize the light reaching the detector 53, without regard for image quality.

The detector 53 is capable of determining the fluorescence from the fluorogenic probes in the sample by converting that fluorescence to a voltage. The detector 53 preferably comprises a photodiode for detecting the fluorescent light. Photodiodes tend to be the smallest and least expensive detection methods. A photodiode detector may be a silicon diode that is photo sensitive. Over a wide range, the amount of light directed into the photodiode detector is directly proportional to the current that the photodiode detector emits. Electronics attached to the photodiode can convert the current to a voltage for input into an analog digital converter, which converts the signal from the detector into a number that may be human or computer readable.

With careful design of the light source, optics, and electronics, photodiodes may be used in the optical module 30. The optical module 30 minimizes the electronics noise though circuit design, cable routing and shielding, using a large electronics gain for the signal from the photodiode, choosing the highest power LEDs available that meet the size constraints of the optical module 30, and optical design that directs as much light as possible to the sample and collects as much light as possible from the sample while simultaneously minimizing the scattered light that is unrelated to the sample.

In other embodiments, other detectors known in the art could be used including, but not limited to, an avalanche photodiode (APD), a photomultiplier tube (PMT), a charge-coupled device (CCD), or similar photodetectors. Avalanche photodiodes typically have faster responses to signals than photodiodes, but require higher voltages to operate and are more expensive. Photomultiplier tubes are typically the most sensitive and the most expensive, and photomultiplier tubes require the highest voltage power supplies. Charge-coupled devices have sensitivity comparable to photodiodes, they provide spatial resolution to the detected light, and they are more expensive than photodiodes.

The electronics of the optical module 30 should be optimized so that its contribution to the noise that limits the sensitivity of the module is as low as possible. Design guidelines that help reach this goal include locating a preamplifier as close as possible to the detector, shielding the optical module from electromagnetic interference, increasing the total electronics gain, and RC filtering the signal.

Optimization of the electronics should occur in concert with optimization of the light source. The light source should produce as stable an illumination as possible.

Once the electronics and light source generate as little noise as possible, the intensity of the light source should be optimized. At low light levels, the detection and electronics noise limits the sensitivity. This noise is independent of light intensity, and because the signal from the optical module 30 increases with increasing light intensity, increasing the light intensity will increase the sensitivity of the optical module 30. At some light intensity level, however, the optical noise (inherent in the generation and detection of the light) will become larger than the electronics noise, and once that intensity is reached, more light intensity will not increase the sensitivity of the optical module 30. The light intensity should be raised as high as possible until the sensitivity of the module no longer increases. Limitations on how high the light intensity can be raised are set by the physical properties of the light source and the space available, as higher power light sources are bigger, require more volume for heat dissipation, and require larger power supplies. Although theoretical modeling helps understand the noise and signal sources, the optimum light intensity is most often determined empirically.

The optical module 30 has the plurality of collection optics 39 completely or partially around the illumination tube 44. The plurality of collection optics 39 surround the aperture 47 of the illumination tube 44 which is located in the center of the plurality of collection optics 39. The plurality of collection optics 39 are located continuously or discretely around the illumination tube 44 to collect and detect the fluorescence in a circular pattern and direct the signal to the detector housing 50 having the detector 53.

Figure 5:
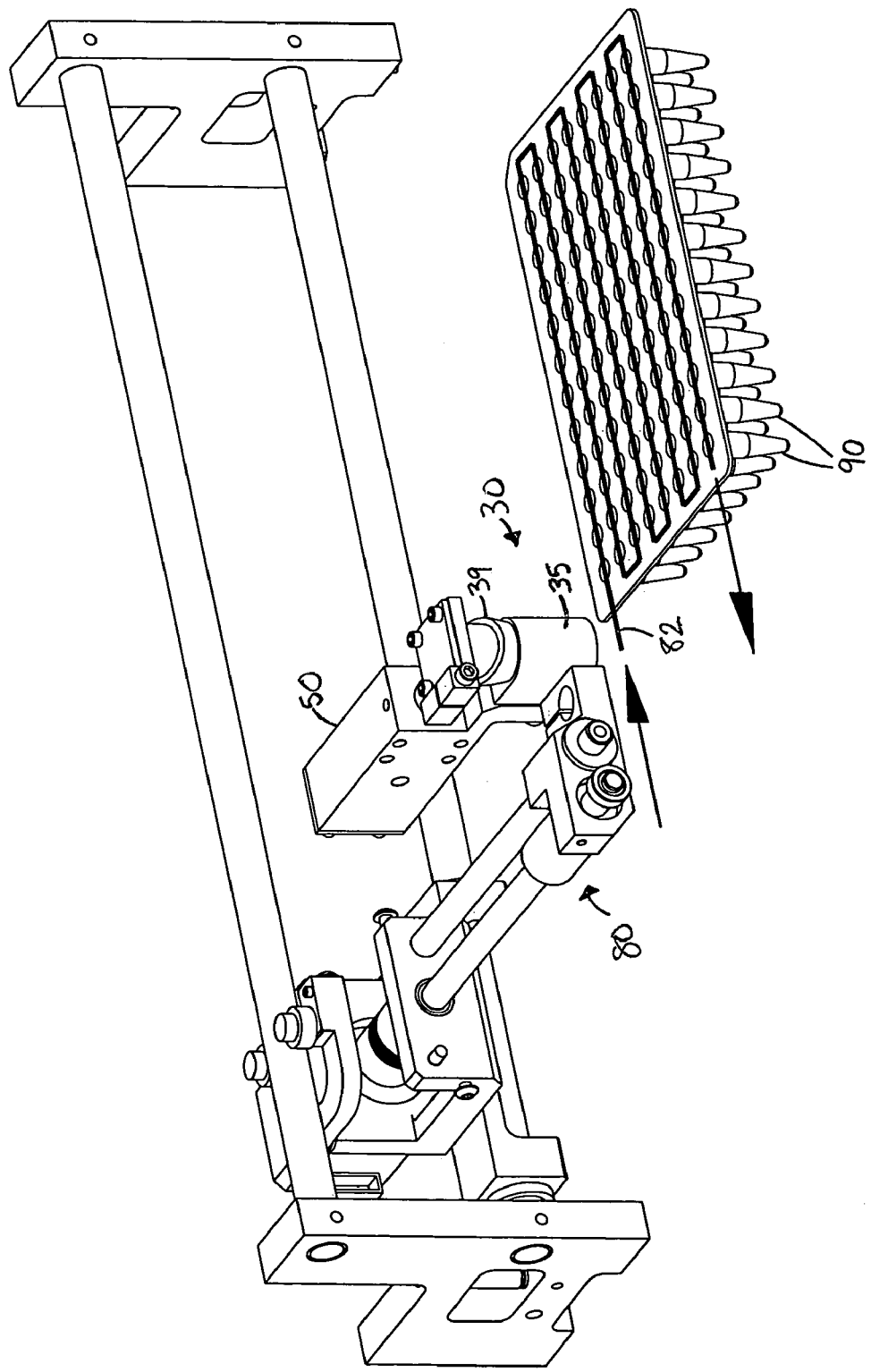
FIG. 5 is a perspective view of an optical module having collection optics located around an illumination tube mounted to an assembly that shows the path as the optical module is scanned over a plurality of sample tubes.

As shown in FIG. 5, the optical module 30 can be used for scanning over the samples of a 96 well (8×12 array) thermal cycler that allows optical access to the samples through caps. FIG. 5 shows a serpentine method for scanning an optical module over an array of samples. The optical module 30 is shown attached to a two-axis motion system 80 that can be controlled by a computer. A path 82 traversed by the optical module 30 can be defined by blind stepping (driving the axes for predefined time periods). Alternatively, the path 82 can be defined through feedback from a sensor or sensors (not shown). Such sensors could be, for example, scales used for measuring the absolute position of the optical module 30 or limit switches set to sense when the optical module 30 is over or at the end of a particular row or column. The path 82 is serpentine and takes the optical module 30 along each row of samples, starting to the left of the left-most sample of a row and ending to the right of the right-most sample of every other row. The motion system 80 then moves the optical module 30 to the next row before scanning the optical module 30 in the opposite direction as the previous row. Although FIG. 5 shows the optical module path over a 96 well thermal cycler, those skilled in the art will recognize that 48 well, 384 well, 1536 well, and other multiple well thermal cyclers are within the spirit and scope of the disclosed embodiments.

In an embodiment, multiple optical modules 30 are packaged together in single unit to scan samples for multiplexing (detection of different fluorogenic probes from the same sample). Each optical module 30 can represent a separate optics channel for a different fluorophore. As the unit with multiple optical modules 30 moves across a plurality of samples, each individual optical module 30 scans the samples sequentially, producing several readings. Having the illumination tube located around the plurality of collection optics minimizes the scattering of light from one optical module 30 into another and increases the combinations of fluorophores that can attain optimal performance, including pairs of fluorophores, one of which has an excitation wavelength close to or the same as the emission wavelength of the other. The multiple optical modules 30 can be connected to a two-axis motion system (shown in FIG. 5) to move across a two-dimensional array of samples. Two, three, four, five, or more optical modules 30 can be packaged together as single unit to interrogate the individual samples. The multiple optical modules can be arranged in straight line one behind each other, in a square, in a parallelogram, in a diamond or other patterns and be within the spirit and scope of the disclosed embodiments.

In an embodiment, the locations of the light source 40 and detector 53 can be switched so fluorescence from the sample is collected in the center of the optical module 30 along the illumination tube 44, and the excitation light reaches the sample from the collection optics. In this embodiment, the excitation light is directed to the sample from the outside, and the fluorescent light emitted from the sample is detected on the inside, along the optical axis. Collecting primarily along the optical axis of the tube could permit preferential selection of a fluorescence from the sample over scattered light from elsewhere, increasing sensitivity. Directing the excitation light from the outside may allow some of the excitation light to not be directed to the sample and escape to be reflected off the corners and edges of the sample cap. The arrangement of the excitation light surrounding the central tube may necessitate using more excitation light to excite the sample.

The optical module having collection optics located around an illumination tube can be used with qPCR instruments of various makes and models, and is not limited to use in an optical module as exemplified in FIGS. 1-5. Other qPCR instruments, systems, and methods of detecting the fluorescence from a qPCR reaction could also benefit from an optical module having collection optics located around an illumination tube. For example, the optical module having collection optics located around an illumination tube could be used with the apparatus for thermally cycling samples of biological material described in assignee's U.S. Pat. No. 6,657,169, and the entirety of this patent is hereby incorporated herein by reference. The optical module having collection optics located around an illumination tube could also be used with the Mx3000P Real-Time PCR System and the Mx4000 Multiplex Quantitative PCR System (commercially available from Stratagene California in La Jolla, Calif.) using a tungsten halogen bulb that sequentially probes each sample, detecting fluorescence with a photomultiplier tube. In addition, the optical module having collection optics located around an illumination tube could be used with qPCR instruments incorporating any or all of the following: a tungsten halogen bulb that sequentially probes each sample; a scanning optical module; stationary samples, light sources, and detectors; stationary LEDs and a detector to probe spinning samples sequentially; and other qPCR instruments known in the art.

The samples of biological material are typically contained in a plurality of sample tubes. The sample tubes are available in three common forms: single tubes; strips of eight tubes attached to one another; and tube trays with 96 attached sample tubes. The optical module 30 is preferably designed to be compatible with any of these three designs.

Each sample tube may also have a corresponding cap for maintaining the biological reaction mixture in the sample tube. The caps are typically inserted inside the top cylindrical surface of the sample tube. The caps are relatively clear so that light can be transmitted through the cap. Similar to the sample tubes, the caps are typically made of molded polypropylene; however, other suitable materials are acceptable. Each cap has a thin, flat, optical window on the top surface of the cap. The optical window in each cap allows radiation such as excitation light to be transmitted to the fluorogenic probes in the samples and emitted fluorescent light from the fluorogenic probes in the samples to be transmitted back to an optical detection system during cycling.

Other sample holding structures such as slides, partitions, beads, channels, reaction chambers, vessels, surfaces, or any other suitable device for holding a sample can be used with the disclosed embodiments. The samples to be placed in the sample holding structure are not limited to biological reaction mixtures. Samples could include any type of cells, tissues, microorganisms, or non-biological materials.

The optical module having collection optics located around an illumination tube can be used for detecting fluorescence in other biological applications including, but not limited to, green fluorescent protein, DNA microarray chips, protein microarray chips, flow cytometry, and similar reactions known to those skilled in the art.

All patents, patent applications, and published references cited herein are hereby incorporated by reference in their entirety. It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A system for detecting fluorescence comprising:
    a light source that emits an excitation light into an illumination tube;
    a plurality of collection optics located around and outside of an aperture in the illumination tube for collecting fluorescence, wherein the plurality of collection optics form a conical shape around the illumination tube; and
    a detector for determining the amount of fluorescence, wherein the illumination tube and collection optics are disposed such that excitation light from the illumination tube and fluorescence collected by the collection optics from a sample are on the same side of the sample, and wherein the system does not comprise a beam splitter.

2. The system of claim 1 further comprising an excitation filter in the illumination tube.

3. The system of claim 1 wherein the plurality of collection optics are fiber optics.

4. The system of claim 1 wherein the plurality of collection optics are light pipes.

5. The system of claim 1 wherein the plurality of collection optics are fluid filled fibers.

6. The system of claim 1 wherein the light source is a light emitting diode.

7. The system of claim 1 wherein the light source is a laser diode.

8. The system of claim 1 wherein the light source is an incandescent light source.

9. The system of claim 1 wherein the detector is a photodiode.

10. The system of claim 1 wherein the detector is an avalanche photodiode.

11. The system of claim 1 wherein the detector is a photomultiplier tube.

12. The system of claim 1 wherein the detector is a charge-coupled device.

13. A detection system for detecting fluorescence from a plurality of samples comprising:
    an illumination tube for receiving an excitation light from a light emitting diode;
    a plurality of collection optics located around and outside of an aperture in the illumination tube for collecting fluorescence, wherein the plurality of collection optics form a conical shape around the illumination tube; and
    a photodiode for detecting the amount of fluorescence,
    wherein the illumination tube and collection optics are disposed such that excitation light from the illumination tube and fluorescence collected by the collection optics from a sample are on the same side of the sample, and wherein the system does not comprise a beam splitter.

14. The system of claim 13 wherein the plurality of collection optics are fiber optics.

15. The system of claim 13 wherein the plurality of collection optics are light pipes.

16. The system of claim 13 wherein the plurality of collection optics are fluid filled fibers.

17. A method for detecting fluorescence comprising:
    emitting an excitation light from a light source into an illumination tube;
    directing the excitation light to an excitation filter;
    illuminating a sample with the excitation light to generate an emission light; and
    detecting the optical characteristics of the emission light using a plurality of collection optics located around and outside of the illumination tube, wherein the plurality of collection optics form a conical shape around the illumination tube,
    wherein the illumination tube and collection optics are disposed such that excitation light from the illumination tube and fluorescence collected by the collection optics from a sample are on the same side of the sample, and wherein the system does not comprise a beam splitter.

* * * * *